United States Patent [19]

Hoelderich et al.

[11] Patent Number: 4,486,617

[45] Date of Patent: Dec. 4, 1984

[54] PREPARATION OF $C_2$–$C_4$-OLEFINS FROM METHANOL/DIMETHYL ETHER

[75] Inventors: Wolfgang Hoelderich; Wolf D. Mross, both of Frankenthal; Matthias Schwarzmann, Limburgerhof, all of Fed. Rep. of Germany

[73] Assignee: BASF Aktiengesellschaft, Fed. Rep. of Germany

[21] Appl. No.: 553,122

[22] Filed: Nov. 18, 1983

[30] Foreign Application Priority Data

Nov. 25, 1982 [DE] Fed. Rep. of Germany ....... 3243520

[51] Int. Cl.³ .................................................. C07C 1/20
[52] U.S. Cl. .................................... 585/640; 585/408; 585/469; 585/733; 502/202
[58] Field of Search ............... 585/640, 408, 469, 733, 585/639; 502/202

[56] References Cited

U.S. PATENT DOCUMENTS

| | | | |
|---|---|---|---|
| 4,254,297 | 3/1981 | Frenken et al. | 585/640 |
| 4,292,458 | 9/1981 | Klotz | 585/640 |
| 4,423,273 | 12/1983 | Hoelderich et al. | 585/640 |
| 4,433,188 | 2/1984 | Hoelderich et al. | 585/640 |

FOREIGN PATENT DOCUMENTS 75203  9/1981  European Pat. Off. ............ 585/640

*Primary Examiner*—Delbert E. Gantz
*Assistant Examiner*—A. Pal
*Attorney, Agent, or Firm*—Keil & Weinkauf

[57] ABSTRACT

$C_2$–$C_4$-olefins are prepared by catalytic conversion of methanol and/or dimethyl ether in the presence of a zeolite catalyst at elevated temperatures by a process wherein the catalyst used is a borosilicate zeolite which is treated with hydrogen fluoride, molded together with an amorphous aluminosilicate as a binder and then treated with hydrochloric acid.

4 Claims, No Drawings

PREPARATION OF $C_2$-$C_4$-OLEFINS FROM METHANOL/DIMETHYL ETHER

Recently, efforts to prepare olefins from methanol have become increasingly important. Methanol can be readily produced from coal, via coal gasification and the production of synthesis gas, with the aid of well-tried technology. If it were possible to convert methanol to lower olefins in an economical manner, the further processing methods which are conventional in the chemical industry today and employ coal as a raw material could also be preserved. In the past few years, processes have therefore been developed with the object of preparing olefins from methanol and/or dimethyl ether.

Such a process is described in, for example, German Laid-Open Application DOS No. 2,615,150. In this process, the catalyst used is a ZSM-5 aluminosilicate zeolite, which is in fact an aromatization catalyst. However, by means of various measures, in particular by reducing the residence time, the conversion can be steered in the direction of olefin formation. Other factors which favor olefin formation are, in particular, dilution of the methanol and the dimethyl ether with an inert gas and steam, respectively, or dilution of the catalyst with a binder. Experience has shown that high olefin yields are obtainable only when methanol and/or dimethyl ether are very substantially diluted with an inert gas or steam. Other conventional processes have the disadvantage that the catalyst can be subjected only to a low load and is rapidly coked. However, there is considerable interest in a simple process which would make it possible to achieve complete conversion of crude methanol and/or dimethyl ether to a hydrocarbon mixture predominantly comprising $C_2$-$C_4$-olefins.

We have found that $C_2$-$C_4$-olefins are obtained in high yield by catalytic conversion of methanol and/or dimethyl ether at elevated temperatures, in the presence of a zeolite catalyst, when the catalyst used is a borosilicate zeolite which is treated with hydrogen fluoride, molded together with an amorphous aluminosilicate as a binder and then treated with hydrochloric acid.

Advantageously, the catalyst used is one in which the borosilicate zeolite is treated with hydrofluoric acid, preferably about 0.1N hydrofluoric acid, and then extruded together with an amorphous aluminosilicate in the ratio 60:40 and the extrudates then treated with hydrochloric acid, preferably with about 18% strength hydrochloric acid. An essential feature of the invention is that the treatment with hydrochloric acid is carried out after the zeolite has been molded together with the binder.

Advantageously, the binders used contain amorphous aluminosilicates whose $SiO_2/Al_2O_3$ ratio is from 35:65 to 75:25% by weight.

A preferred method of preparing the catalyst used according to the invention comprises calcining the zeolite and then treating it with 0.001-1N, preferably 0.05-0.2N, HF for from 1 to 3 hours at from 60° to 80° C. The product is filtered off, washed, dried at from 100° to 140° C. and calcined at from 500° to 600° C. The borosilicate zeolite treated in this manner is extruded with an amorphous aluminosilicate, whose $SiO_2/Al_2O_3$ ratio is from 35:65 to 75:25% by weight, preferably 75:25% by weight, the ratio of borosilicate zeolite to aluminosilicate be. 60:40; the extrudates are again calcined at from 500° to 600° C. After extrusion with the binder, the catalyst is treated with a 3-25, in particular 12-20, % strength hydrochloric acid for a further 1-3 hours at from 60° to 80° C. and is then calcined for 5 hours at from 500° to 600° C.

In carrying out the process, methanol and/or dimethyl ether are converted over the catalysts described above, under a pressure of from atmospheric pressure to about 30 bar, preferably from 0 to 1 bar, and at from 300° to 650° C., preferably from 400° to 550° C. The methanol may contain as much as 90% by weight of water, but it is advantageous to use, as the starting material, crude methanol which contains about 20% of water.

Other lower alcohols may also be admixed to the methanol. The catalyst load, expressed as WHSV in $h^{-1}$, ie. g of methanol and/or dimethyl ether per g of catalyst per hour, is advantageously chosen such that high quantitative conversion of the starting materials takes place, so that separation and recycling problems with regard to unconverted dimethyl ether do not arise. In general, therefore, the WHSV should be from 0.5 to 50 $h^{-1}$, preferably from 2 to 15 $h^{-1}$.

The novel process results in a substantial increase in the selectivity with respect to $C_2$-$C_4$-olefins in the conversion of methanol to hydrocarbons, in particular at from 400° to 600° C.

Another advantage of the novel process is the increase in the time-on-stream of the catalyst used. The time-on-stream is the time between successive regenerations. The overall service life of the catalyst is also increased. The improvement in the time-on-stream as a result of the invention is particularly important in the conversion at elevated temperatures, for example at from 450° to 550° C.

The formation of the undesirable by-products methane and aromatics is substantially suppressed. Another advantage of the invention is that when the conversion to $C_2$-$C_4$-olefins is carried out using crude methanol the addition of inert diluents, eg. $N_2$, He or $H_2O$ can be dispensed with.

The Example which follows illustrates the process according to the invention.

EXAMPLE

Catalyst A (according to the invention)

The boron zeolite is synthesized hydrothermally from 64 g of $SiO_2$ (Aerosil 200), 12.2 g of $H_3BO_3$, and 800 g of an aqueous 1,6-hexanediamine solution (50:50 mixture) at 170° C. under autogenous pressure in a stirred autoclave. The crystalline product is filtered off, washed, dried for 24 hours at 110° C. and calcined for 24 hours at 500° C. This borosilicate zeolite is composed of 94.2% by weight of $SiO_2$ and 2.32% by weight of $B_2O_3$.

50 g of this borosilicate zeolite are refluxed with 140 ml of 0.1N HF for 1 hour. The product is filtered off, washed with water, dried for 16 hours at 110° C. and calcined for 5 hours at 500° C. It is then extruded together with amorphous aluminosilicate ($SiO_2$:$Al_2O_3$=75%:25%) in the ratio 60:40, and the extrudates are dried for 16 hours at 110° C. and calcined for 16 hours at 500° C. 50 g of these catalyst extrudates are refluxed with 200 ml of 18% strength HCl for 1 hour. The catalyst is then washed chloride-free, dried for 16 hours at 110° C. and calcined for 5 hours at 500° C.

Crude methanol containing 20% by weight of water is converted quantitatively over this catalyst A under isothermal conditions, in a tube reactor, at 500° C. and a WHSV of 7.8 h$^{-1}$ (based on CH$_3$OH employed). The yields, based on CH$_2$ employed, are shown in column A of the Table.

To compare yields, the following catalysts were employed; they were tested under the same reaction conditions as in the case of catalyst A.

Catalyst B is obtained by extruding the borosilicate zeolite described above with boehmite in the ratio 60:40. Drying is carried out at 110° C. for 16 hours and calcining at 500° C. for 16 hours.

Catalyst C is obtained by refluxing 70 g of catalyst B with 465 ml of 18% strength hydrochloric acid for 1 hour, washing the product chloride-free with water, drying it at 110° C. for 16 hours and then calcining it at 500° C. for 5 hours. This catalyst corresponds to catalyst A without HF treatment and without extrusion with amorphous aluminosilicate.

Catalyst D is prepared by extruding 72 g of the above borosilicate zeolite with 48 g of an amorphous aluminosilicate composed of 75% of SiO$_2$ and 25% of Al$_2$O$_3$. The 2 mm extrudates are calcined at 110° C. for 16 hours. 42 g of these extrudates are refluxed with 200 ml of 18% strength hydrochloric acid for 1 hour, and the product is washed chloride-free, dried at 110° C. and then heated at 500° C. for 5 hours.

This catalyst corresponds to catalyst A without HF treatment and HCl treatment.

Catalyst E corresponds to catalyst A without HCl treatment.

The comparison in the Table shows that the novel catalyst A gives the best yields of C$_2$–C$_4$-olefins.

TABLE

| Composition of the product | Catalyst A | Comparative catalysts | | | |
|---|---|---|---|---|---|
| | | B | C | D | E |
| CH$_4$ % | 0.9 | 5.4 | 2.5 | 1.1 | 1.5 |
| C$_2$H$_4$ % | 5.3 | 7.0 | 7.3 | 4.9 | 7.4 |
| C$_2$H$_6$ % | — | 0.5 | 0.2 | 0.1 | 0.2 |
| C$_3$H$_6$ % | 47.1 | 31.4 | 41.8 | 41.9 | 42.2 |
| C$_3$H$_8$ % | 0.6 | 1.6 | 1.0 | 0.6 | 1.1 |
| C$_4$H$_8$ % | 26.6 | 17.6 | 21.8 | 22.7 | 24.1 |
| C$_4$H$_{10}$ % | 1.3 | 1.8 | 1.0 | 1.2 | 1.7 |
| C$_5$+-aliphatics | 16.2 | 18.9 | 17.9 | 20.8 | 15.2 |
| C$_6$+-aromatics | 1.0 | 13.8 | 5.4 | 4.7 | 1.4 |
| Time-on-stream h | 132 | 12 | 77 | 25 | 53 |
| g of CH$_3$OH/g of catalyst | 1030 | 94 | 600 | 195 | 413 |

We claim:

1. A process for the preparation of C$_2$–C$_4$-olefins by catalytic conversion of methanol and/or dimethyl ether in the presence of a zeolite catalyst at elevated temperatures, wherein the catalyst used is a borosilicate zeolite which is treated with hydrogen fluoride, molded together with an amorphous aluminosilicate as a binder and then treated with hydrochloric acid.

2. A process as claimed in claim 1, wherein 0.001–1N hydrogen fluoride is used in the treatment of the borosilicate zeolite.

3. A process as claimed in claim 1, wherein the binder used for molding is an amorphous aluminosilicate whose SiO$_2$/Al$_2$O$_3$ ratio is from 35:65 to 75:25.

4. A process as claimed in claim 1, wherein from 3 to 25% strength hydrochloric acid is used in the final treatment of the catalyst.

* * * * *